United States Patent [19]

Kreyenhagen et al.

[11] Patent Number: 5,282,836
[45] Date of Patent: Feb. 1, 1994

[54] ATRIAL DEFIBRILLATOR AND METHOD FOR PROVIDING PRE-CARDIOVERSION PACING

[75] Inventors: Paul E. Kreyenhagen, Bellevue; Kenneth R. Infinger, Redmond, both of Wash.

[73] Assignee: InControl, Inc., Redmond, Wash.

[21] Appl. No.: 965,167

[22] Filed: Oct. 23, 1992

[51] Int. Cl.⁵ .................... A61N 1/39; A61N 1/362
[52] U.S. Cl. .................................................. 607/4
[58] Field of Search .............................. 607/4, 5, 2, 14

[56] References Cited

U.S. PATENT DOCUMENTS

| | | | |
|---|---|---|---|
| 3,738,370 | 6/1973 | Charms | 128/419 D |
| 3,952,750 | 4/1976 | Mirowski et al. | 128/419 D |
| 5,014,698 | 5/1991 | Cohen | 128/419 D |
| 5,074,301 | 12/1991 | Gill | 607/4 |
| 5,165,403 | 11/1992 | Mehra | 128/419 D |

*Primary Examiner*—William E. Kamm
*Assistant Examiner*—Kennedy J. Schaetzle
*Attorney, Agent, or Firm*—Foley & Lardner

[57] ABSTRACT

An implantable atrial defibrillator provides cardioverting electrical energy to the atria of a human heart in need of cardioversion. The atrial defibrillator includes a first detector for detecting atrial activity of the heart and an atrial fibrillation detector responsive to the first detector for determining when the atria of the heart are in need of cardioversion. The atrial defibrillator further includes a pacing output circuit responsive to the atrial fibrillation detector for pacing the ventricles of the heart at a pacing rate when the atria of the heart are in need of cardioversion and a cardioverter stage for applying the cardioverting electrical energy to the atria of the heart after the pacing output circuit has paced the ventricles for a predetermined number of cardiac cycles. The pacing output circuit stabilizes the cardiac rate of the heart prior to the application of the cardioverting electrical energy.

44 Claims, 4 Drawing Sheets

ATRIAL DEFIBRILLATOR AND METHOD FOR PROVIDING PRE-CARDIOVERSION PACING

BACKGROUND OF THE INVENTION

The present invention generally relates to an atrial defibrillator and method for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation which may result from the delivery of cardioverting electrical energy to the atria. More specifically, the atrial defibrillator and method of the present invention guards against applying cardioverting electrical energy to the atria under conditions believed to contribute to induced ventricle fibrillation.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

Improved atrial defibrillators and lead systems which exhibit both automatic operation and improved safety are fully described in copending U.S. application Ser. No. 07/685,130, filed Apr. 12, 1991, in the names of John M. Adams and Clifton A. Alferness for IMPROVED ATRIAL DEFIBRILLATOR AND METHOD and Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. As disclosed in the aforementioned referenced applications, synchronizing the delivery of the defibrillating or cardioverting electrical energy to the atria with a ventricular electrical activation (R wave) of the heart has been considered important to avoid cardioverting the heart during the heart's vulnerable period or T wave to thus prevent induced ventricular fibrillation. Ventricular fibrillation is a fatal arrhythmia which can be caused by electrical energy being delivered to the heart at the wrong time in the cardiac cycle, such as during the T wave of the cycle. The atrial defibrillators of the aforementioned referenced applications exhibit improved safety from inducing ventricular fibrillation by sensing ventricular activations of the heart in a manner which avoids detecting noise as ventricular electrical activations for generating reliable synchronization signals. Hence, these implantable atrial defibrillators, by providing such noise immunity in R wave detection assure reliable synchronization.

Another measure for reducing the risk of inducing ventricular fibrillation during the delivery of cardioverting electrical energy to the atria of the heart employed by the defibrillators of the aforementioned referenced applications is the reduction of the amount of the electrical energy which is passed through the ventricles during cardioversion of the atria. This is achieved by locating the cardioverting electrodes in or near the heart to provide a cardioverting energy path which confines most of the cardioverting electrical energy to the atria of the heart.

It has also been observed that during episodes of atrial fibrillation, the cardiac rate often becomes highly variable. The highly variable cardiac rate is generally characterized by repetitively alternating long and short cardiac cycles which result in dispersion of refractoriness. With such highly variable cardiac rates, there can be a dispersion of refractoriness after the long cardiac cycles. This creates an increased sensitivity to an "R on T" condition contributing to the likelihood of induced ventricular fibrillation if the atria are cardioverted in synchronism with an R wave which is closely adjacent to the preceding T wave.

The atrial defibrillator and method of the present invention greatly reduces the risk of inducing ventricular fibrillation during atrial cardioversion or defibrillation by assuring that the cardioverting electrical energy is not applied to the atria during a time of dispersion of refractoriness. As will be seen hereinafter, this is accomplished by stabilizing the heart rate through pacing the ventricles at a constant or fixed cardiac rate before the cardioverting or defibrillating electrical energy is applied to the atria of the heart. Such heart rate stabilization prevents a dispersion of refractoriness condition from occurring. Furthermore, the cardioverting electrical energy is preferably applied at a time corresponding to the fixed cardiac rate while the ventricles are also paced. This assures that the cardioverting electrical energy is applied in synchronism with depolarization of the ventricles and not during a T wave. As a result, a reduced risk of induced ventricular fibrillation is assured because the cardioverting electrical energy will not be applied to the atria during an R on T condition or during a vulnerable period of the heart.

SUMMARY OF THE INVENTION

The present invention therefore provides an implantable atrial defibrillator for providing cardioverting electrical energy to the atria of a human heart in need of cardioversion. The atrial defibrillator includes first detecting means for detecting atrial activity of the heart and atrial fibrillation detecting means responsive to the first detecting means for determining when the atria of the heart are in need of cardioversion. The atrial defibrillator further includes stabilizing means responsive to the atrial fibrillation detecting means for stabilizing the cardiac rate of the heart when the atria of the heart are in need of cardioversion and cardioverting means for applying the cardioverting electrical energy to the atria of the heart after the stabilizing means has stabilized the cardiac rate for a predetermined number of cardiac cycles.

The present invention further provides a method of applying cardioverting electrical energy to the atria of a human heart in need of cardioversion. The method includes the steps of detecting atrial activity of the heart, and determining when the atria of the heart are in need of cardioversion. The method further includes the step of stabilizing the cardiac rate of the heart when the atria of the heart are in need of cardioversion, and applying the cardioverting electrical energy to the atria of the heart after stabilizing the cardiac rate of the heart for a predetermined number of cardiac cycles.

The present invention still further provides an implantable atrial defibrillator for providing cardioverting electrical energy to the atria of a human heart in need of cardioversion. The atrial defibrillator includes first detecting means for detecting atrial activity of the heart and atrial fibrillation detecting means responsive to the first detecting means for determining when the atria of the heart are in need of cardioversion. The atrial defibrillator further includes pacing means responsive to the atrial fibrillation detecting means for pacing the ventricles of the heart at a pacing rate when the atria of the heart are in need of cardioversion and cardioverting means for applying the cardioverting electrical energy to the atria of the heart after the pacing means has paced the ventricles for a predetermined number of cardiac cycles.

The present invention still further provides a method of applying cardioverting electrical energy to the atria of a human heart in need of cardioversion. The method includes the steps of detecting atrial activity of the heart, and determining when the atria of the heart are in need of cardioversion. The method further includes the step of pacing the ventricles of the heart at a pacing rate when the atria of the heart are in need of cardioversion, and applying the cardioverting electrical energy to the atria of the heart after pacing the ventricles of the heart for a predetermined number of cardiac cycles.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
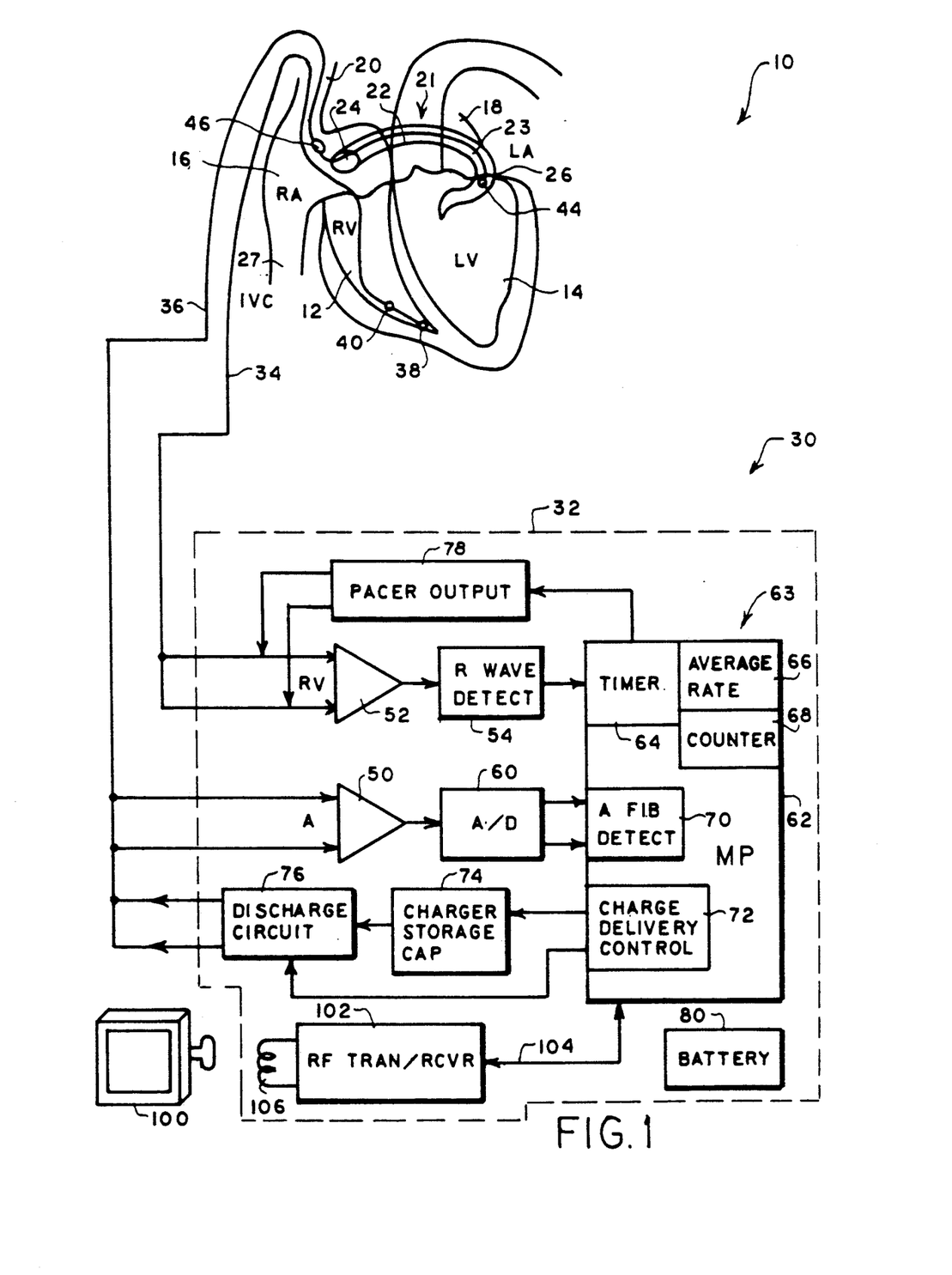
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Prior to referring to FIG. 1, a general description of a typical electrocardiogram (ECG) cycle may be helpful in understanding the operation and various aspects of the present invention. The ECG cycle begins with a P wave which is normally a small positive wave. The P wave indicates depolarization of the atria of the heart. Following the P wave there is an ECG portion which is substantially constant in amplitude. The P wave and this substantially constant portion will have a time duration on the order of, for example, 120 milliseconds.

The QRS complex of the ECG then normally occurs after the substantially constant portion. The dominating feature of the QRS complex is the R wave which is a rapid positive deflection. The R wave generally has an amplitude greater than any other wave of the ECG and will have a spiked shape of relatively short duration with a sharp rise, a peak amplitude, and a sharp decline. The R wave indicates depolarization or activation of the ventricles and hence, as used herein, the term "ventricle activations" denotes R waves of the heart cardiac cycles.

Following the QRS complex, the ECG is completed with the T wave which is separated from the QRS complex by about 250 milliseconds. The T wave is relatively long in duration of, for example, on the order of 150 milliseconds. It is during the T wave that the heart is most vulnerable to induced ventricular fibrillation should the heart be cardioverted during this period. The next ECG cycle begins with the next P wave. The duration of a cardiac cycle may be on the order of 800 milliseconds.

As will be appreciated by those skilled in the art, the ECG characteristics of a heart experiencing atrial fibrillation will be distinctly different than described above for a heart in normal sinus rhythm. During atrial fibrillation, there generally are no discernable P waves because the atria are in an unstable or fluttering condition. Also, the cardiac rate may be highly variable which results in the previously referred to dispersion of refractoriness condition. As used herein, the term "cardiac cycle" denotes the period of heart activity which begins with each ventricular activation (R wave) of the heart.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of ventricular activations in the right ventricle. The electrodes 38 and 40 further provide for pacing the ventricles 12 and 14 in a manner to be described hereinafter in accordance with the present invention. As illustrated, the lead 34 is fed through the inferior vena cava 27, into the right atrium 16, and then into the right ventricle 12 as illustrated. As will be appreciated by those skilled in the art, a second path for lead 34 could alternatively be through the superior vena cava 20, into the right atrium 16, and then into the right ventricle 12.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the eft ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, a second sense amplifier 52, and an R wave detector 54. The first sense amplifier 50 forms a first detecting means which, together with the lead 36 to which sense amplifier 50 is coupled, senses atrial activity of the heart. The second sense amplifier 52 and the R wave detector 54 form a second detecting means which, together with the lead 34 to which sense amplifier 52 is coupled, detects ventricular activations of the right ventricle of the heart.

The output of the second sense amplifier 52 is coupled to the R wave detector 54. The R wave detector 54 is of the type well known in the art which provides an output pulse upon the occurrence of an R wave being sensed during a cardiac cycle of the heart.

The output of the first sense amplifier 50 is coupled to an analog to digital converter 60. The analog to digital converter 60 which converts the analog signal representative of the atrial activity of the heart being detected to digital samples for further processing in a manner to be described hereinafter.

The enclosure 32 of the atrial defibrillator 30 further includes a microprocessor 62. The microprocessor 62 is preferably implemented in a manner as disclosed in the aforementioned copending U.S. application Ser. No. 07/685,130 and 07/856,514 and further as described hereinafter with respect to the flow diagrams of FIGS. 2-4. The implementation of the microprocessor 62 in accordance with this embodiment of the present invention results in a plurality of functional stages. The stages include a timer 64, an average rate stage 66, a counter stage 68, an atrial arrhythmia detector in the form of an atrial fibrillation detector 70, and a charge delivery and energy control stage 72.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and coveys the data to the memory 92 over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, the microprocessor 62 receives programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in interval memory or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 74 of the type well known in the art which charges a storage capacitor to a predetermined voltage level, a discharge circuit 76 for discharging the storage capacitor within circuit 74 by a predetermined amount to provide a controlled discharge output of electrical energy when required to the atria of the heart, and a pacer output circuit 78 for applying pacing electrical energy to the ventricles of the heart.

The discharge circuit 76 is coupled to the first electrode 44 and the second electrode 46 of the second lead 36. This permits the application of the cardioverting or defibrillating electrical energy to the atria.

The pacer output circuit 78 may be of the type well known in the art for providing pacing electrical energy. The pacer output circuit 78 is coupled to electrodes 38 and 40 of lead 34 for applying the pacing electrical energy to the right ventricle 12. As will be seen hereinafter, the pacer output circuit 78 together with the timer 64, average rate stage 66 and counter 68 form a cardiac rate stabilizer 63 for stabilizing the cardiac rate of the heart when the atria are in need of cardioversion and before cardioverting electrical energy is applied to the atria.

Lastly, the defibrillator 30 includes a depletable power source 80, such as a lithium battery. The battery 80 provides power to the electrical components of the atrial defibrillator 30.

The sense amplifier 52 and the R wave detector 54 continuously detect the occurrence of ventricular activations of the right ventricle 12. As disclosed in the aforementioned copending U.S. applications Ser. Nos. 07/685,130 and 07/856,514, incorporated herein by reference, when the time intervals between immediately successive R waves indicate the probability of an episode of atrial fibrillation, the microprocessor 62 enables the atrial fibrillation detector 70, sense amplifier 50, and the analog to digital converter 60. Further, in accordance with this preferred embodiment, the microprocessor also resets counter 68 and then enters the routine illustrated in the flow diagram of FIG. 2.

Figure 2:
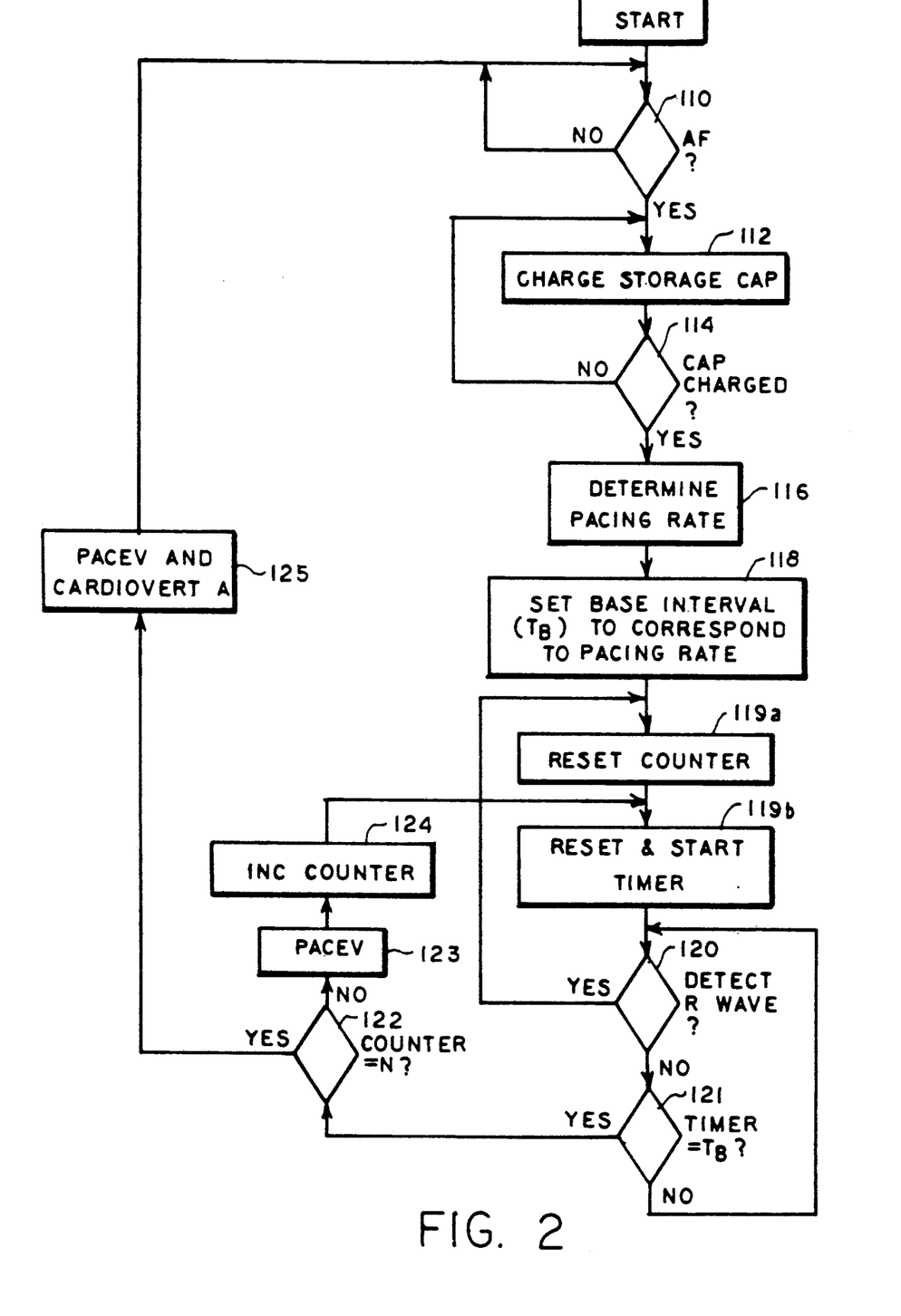
FIG. 2 is a flow diagram illustrating the manner in which the atrial defibrillator of FIG. 1 may be implemented in accordance with a first embodiment of the present invention for applying defibrillating or cardioverting electrical energy to the atria of the heart with reduced risk of inducing ventricular fibrillation.

Referring now to FIG. 2, the microprocessor 62 first determines, in step 110, if the heart is experiencing an episode of atrial fibrillation. In performing step 110, the microprocessor 62 may implement any one of the algorithms identified in the aforementioned cross-referenced copending applications incorporated herein by reference. If the atrial fibrillation detector 70 does not detect an episode of atrial fibrillation, the microprocessor will continue to implement the algorithm. When the atrial fibrillation detector 70 determines that the heart is experiencing an episode of atrial fibrillation, the microprocessor then, in step 112, causes the charge delivery and control stage 72 to initiate the storage of the cardioverting electrical energy within the storage capacitor of charger and storage capacitor circuit 74. The microprocessor thereafter, at periodic intervals, determines in step 114 if the storage capacitor is fully charged. If it is not, it continues to cause the charge delivery and control stage 72 to charge the storage capacitor. When the storage capacitor is fully charged, the microprocessor then advances to step 116 to determine a pacing rate for the heart. An appropriate pacing rate may be a rate that corresponds to the average cardiac rate. In performing step 116 to determine the average cardiac rate, the microprocessor utilizes the timer 64 and the average rate stage 66. The timer 64 times the intervals between ventricular activations of the heart detected by the sense amplifier 52 and the R wave detector 54. After a preselected number of cardiac cycles, for example, 10 to 20 cardiac cycles, the average rate stage 66 determines the average rate of the preselected number of cardiac cycles.

The microprocessor then proceeds to 118 and sets the base interval, which will be utilized to pace the heart, to correspond to the average cardiac rate determined in step 116. The base interval, by being based upon the average cardiac rate of the last preselected number of cardiac cycles, will be appropriate for obtaining capture of the heart upon such pacing.

The microprocessor then proceeds to serial steps 120 and 121 to determine if a ventricular activation (R wave) has been detected by the sense amplifier 52 and the R wave detector 54 before the timer 64 has timed the base interval ($T_B$). If a ventricular activation is detected before timer 64 equals $T_B$, the microprocessor returns to steps 119a and 199b and resets the counter 68 and timer 64. If not ventricular activation is detected before timer 64 equals the base interval $T_B$, the microprocessor proceeds to step 122 and determines if counter 68 equals a predetermined number of counts (N). If the counter does not equal N, the microprocessor will cause the pacer output 78 to pace the ventricles in step 123 and will increment the counter in step 124.

The microprocessor then performs steps 119b, 120, 121 and 122 as previously described. When the microprocessor determines, in step 122, that the counter 68 equals the predetermined number of counts (N), the cardiac rate of the heart will have been stabilized by being paced at a constant cardiac rate corresponding to the base interval for a predetermined number of consecutive cardiac cycles. In accordance with the preferred embodiment, the predetermined number of consecutive cardiac cycles for which the heart is paced is equal to eight cardiac cycles.

It can be seen that steps 119b, 120, 121 and 123 form the fundamental basis of demand mode pacing and more specifically, VVI mode pacing. Although VVI mode is described, other pacing modes are possible without departing from the present invention.

Now that the heart has been paced for the predetermined number of cardiac cycles as described above, the atrial defibrillator 30 is ready to apply cardioverting electrical energy to the atria 16 and 18 of the heart. The microprocessor in step 125 causes the pacer output 78 to apply the pacing electrical energy to the ventricles coincident with causing the discharge circuit 76 to discharge the storage capacitor of circuit 74 for applying the cardioverting electrical energy to electrodes 44 and 46 of the lead 36. As a result, the cardioverting electrical energy is applied to the atria of the heart and, coincident therewith, the pacing electrical energy is applied to the ventricles. When step 134 is completed, the microprocessor then returns.

Figure 3:
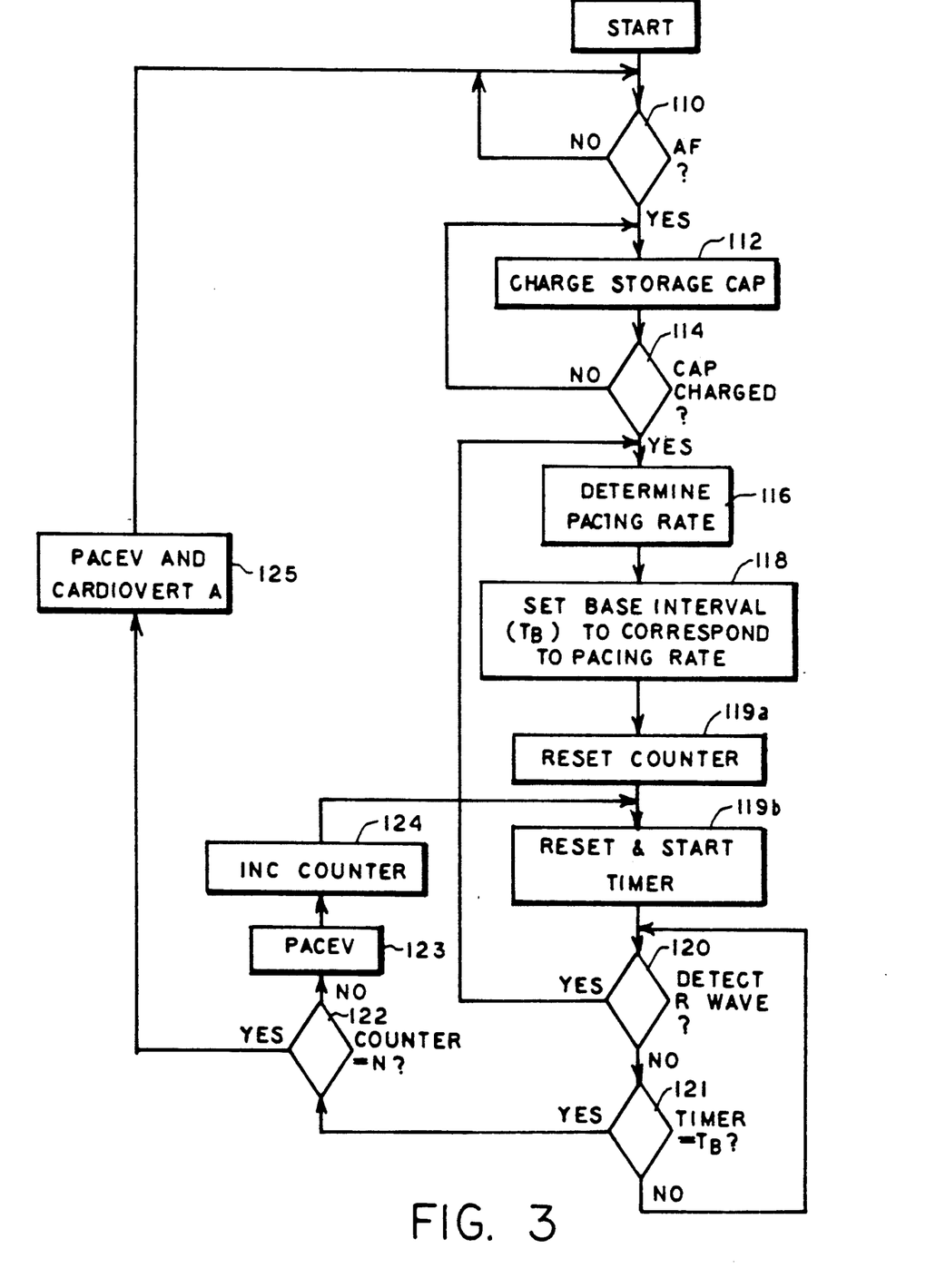
FIG. 3 is a flow diagram illustrating another manner in which the atrial defibrillator of FIG. 1 may be implemented in accordance with a second embodiment of the present invention.

Referring now to FIG. 3, it illustrates a manner of implementation similar to that illustrated in FIG. 2. However, as can be noted in FIG. 3, instead of returning to step 119a after detecting a ventricular activation prior to timer 64 timing the base interval $T_B$, the microprocessor returns to step 116 to determine a new base interval. Since an unpaced cardiac cycle will be shorter than the then prevailing base interval, the new base interval determined by the average rate stage will be shorter than the prior base interval. Hence, for each unpaced cardiac cycle, the average rate stage will incrementally or slightly increase the pacing rate. This adaptive process of controlling the pacing rate increases the probability of capturing the heart for pacing the heart for the predetermined number of consecutive paced cardiac cycles. Although not illustrated in FIG. 3, an additional step may be included in the flow diagram to set an upper limit on the pacing rate so as to avoid causing a possible R on T condition.

Figure 4:
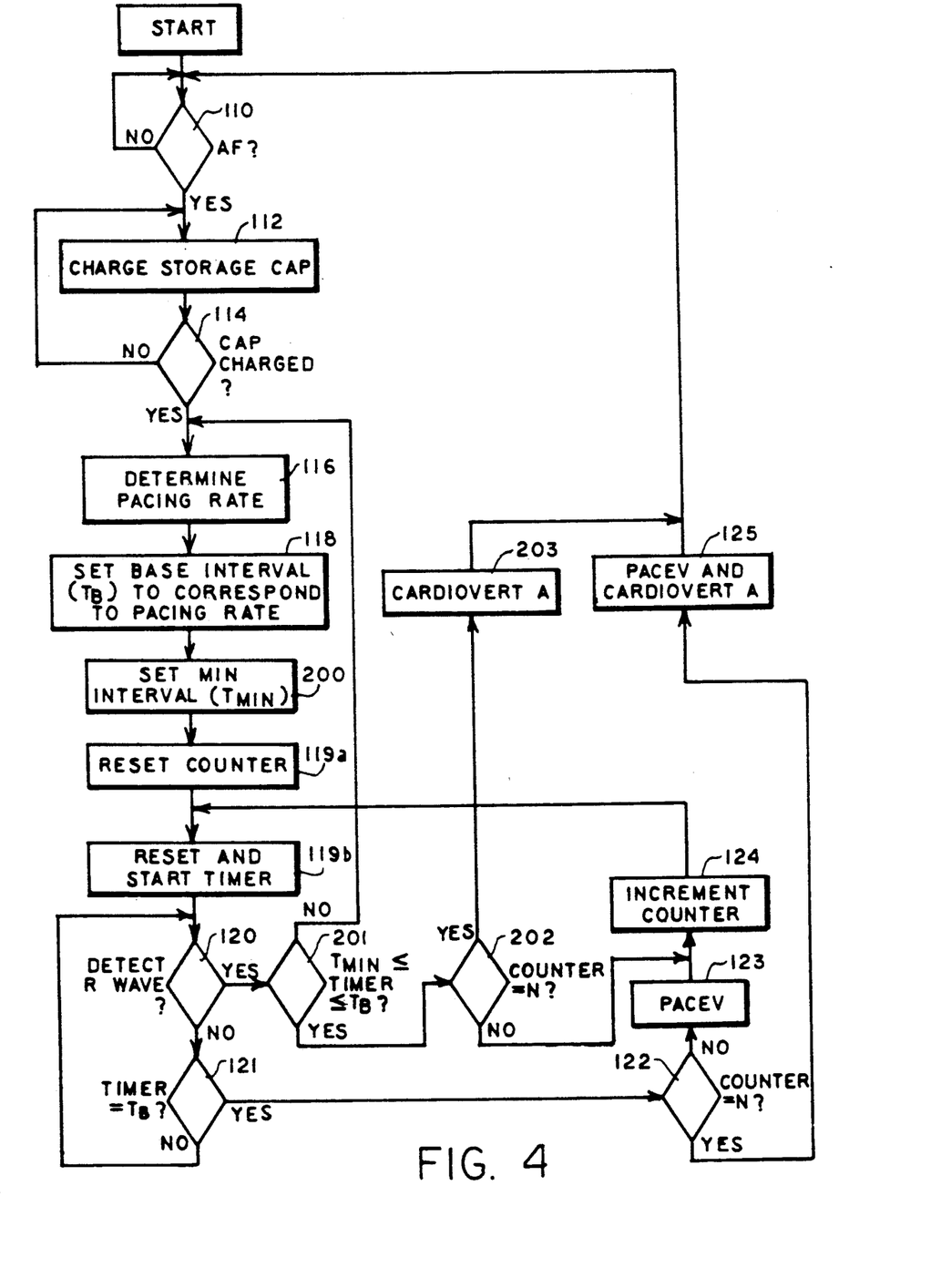
FIG. 4 is a flow diagram illustrating still another manner in which the atrial defibrillator of FIG. 1 may be implemented in accordance with a third embodiment of the present invention.

Referring now to FIG. 4, it is a flow diagram illustrating another manner in which the atrial defibrillator of FIG. 1 may be implemented in accordance with a third embodiment of the present invention. The flow diagram of FIG. 4 is similar to the flow diagram of FIG. 2 except it includes additional steps 200, 201, 202, and 203 to be described hereinafter. With these additional steps, the atrial defibrillator establishes an interval window to enable unpaced cardiac cycle having intervals substantially equal to the base interval (within ten percent of the base interval) to be counted in the same manner as the paced cardiac cycles. Hence, in accordance with this embodiment, the predetermined number of cardiac cycles in which the cardiac rate is stabilized before cardioversion will equal the sum of the number of paced cardiac cycles plus the number of cardiac cycles having intervals substantially equal to the base interval. As in the previous embodiments, the predetermined number of cardiac cycles in which the cardiac rate is stabilized before cardioversion are consecutive cardiac cycles.

Referring now more specifically to FIG. 4, it will be noted that after setting the base interval $T_B$ to correspond to the pacing rate in step 118, the microprocessor next in step 200 sets a minimum interval ($T_{MIN}$). The minimum interval may be, for example, ninety percent of the base interval. As an example, if the base interval is one second, the minimum interval will be 900 milliseconds.

It will be further noted that if an R wave is detected in steps 120 and 121 before the timer 64 equals the base interval ($T_B$), the microprocessor 62 determines in step 201 if the interval of t his cardiac cycle was between the minimum interval ($T_{MIN}$) and the base interval ($T_B$). If it was, the microprocessor next determines in step 202 if the counter equals the predetermined number of counts (N). If it does, the microprocessor 62 then causes the discharge circuit 76 to apply the cardioverting electrical energy to the atria in step 203. It will be noted that the ventricles are not paced at this time in view of the already sensed R wave.

If the counter does not equal N in step 202, the microprocessor 62 will proceed to step 124 to increment the counter 68. It then, in step 119b, resets and starts timer 64 for timing the next cardiac cycle.

If the R wave was determined in step 201 to have occurred before the minimum interval expired, the microprocessor will go from step 201 to step 116 to determine a new pacing rate as previously described with respect to FIG. 3. It should also be noted that in doing so, a new minimum interval will be determined in step 200 and that the counter will be reset in step 119a.

As can thus be seen, the present invention provides a new and improved implantable atrial defibrillator for applying cardioverting electrical energy to the atria of a heart in need of cardioversion in a manner which substantially reduces the risk of inducing ventricular fibrillation as a result of the application of the cardioverting electrical energy to the atria of the heart. To that end, the atrial defibrillator of the present invention, after determining that the heart is in need of cardioversion, first stabilizes the cardiac rate of the heart by pacing the ventricles of the heart for a predetermined number of cardiac cycles or as required for a predetermined number of cardiac cycles to stabilize the cardiac rate prior to applying the cardioverting electrical energy to the atria. The stabilization of the cardiac rate of the heart prior to cardioversion precludes cardioverting the heart when the cardiac rate of the heart is highly variable and thus susceptible of experiencing an R on T condition during dispersed ventricular refractoriness. Improved safety is further provided by applying the cardioverting electrical energy at a time corresponding to the rate in which the heart had been paced. Further safety is provided by also pacing the ventricles if required when the cardioverting electrical energy is applied to the heart. Hence, the cardioverting energy is applied coincident with a ventricular activation to further assure that the cardioverting electrical energy is not applied during the vulnerable period of the heart. The cardiac rate in which the ventricles are paced is made equal to a rate likely to capture the ventricles. This may be the average rate in the absence of pacing, or a programmed rate, or another calculated rate.

While particular embodiments of the present invention have been shown and described, modifications may be made, and it is therefore intended to cover in the appended claims all such changes and modifications which fall within the true spirit and scope of the invention.

What is claimed is:

1. An implantable atrial defibrillator for providing cardioverting electrical energy to the atria of a human heart in need of cardioversion, said atrial defibrillator comprising:
   first detecting means for detecting atrial activity of the heart;
   atrial fibrillation detecting means responsive to said first detecting means for determining when the atria of the heart are in need of cardioversion;
   stabilizing means responsive to said atrial fibrillation detecting means for stabilizing the cardiac rate of the heart when the atria of the heart are in need of cardioversion; and
   cardioverting means for applying the cardioverting electrical energy to the atria of the heart after said stabilizing means has stabilized the cardiac rate for a predetermined number of cardiac cycles.

2. An atrial defibrillator as defined in claim 1 wherein said stabilizing means includes pacing means for pacing the ventricles of the heart.

3. An atrial defibrillator as defined in claim 2 wherein said cardioverting means applies the cardioverting electrical energy to the atria of the heart after said pacing means has paced the ventricles for a predetermined number of cardiac cycles.

4. An atrial defibrillator as defined in claim 3 wherein said predetermined number of cardiac cycles are consecutive paced cardiac cycles.

5. An atrial defibrillator as defined in claim 2 wherein said pacing means paces the ventricles of the heart at a pacing rate and in a demand mode.

6. An atrial defibrillator as defined in claim 5 wherein said demand mode is a VVI mode.

7. An atrial defibrillator as defined in claim 5 further including means for increasing said pacing rate responsive to an unpaced cardiac cycle.

8. An atrial defibrillator as defined in claim 5 further including timing means for timing the intervals of the cardiac cycles of the heart and wherein said predetermined number of cardiac cycles is the sum of paced cardiac cycles plus unpaced cardiac cycles having intervals substantially equal to a base interval corresponding to said pacing rate.

9. An atrial defibrillator as defined in claim 8 wherein said unpaced cardiac cycles have intervals between said base interval and ninety percent of said base interval.

10. An atrial defibrillator as defined in claim 8 wherein said predetermined number of cardiac cycles are consecutive cardiac cycles.

11. An implantable atrial defibrillator for providing cardioverting electrical energy to the atria of a human heart in need of cardioversion, said atrial defibrillator comprising:
first detecting means for detecting atrial activity of the heart;
atrial fibrillation detecting means responsive to said first detecting means for determining when the atria of the heart are in need of cardioversion;
pacing means responsive to said atrial fibrillation detecting means for pacing the ventricles of the heart at a pacing rate when the atria of the heart are in need of cardioversion; and
cardioverting means for applying the cardioverting electrical energy to the atria of the heart after said pacing means has paced the ventricles for a predetermined number of paced cardiac cycles.

12. An atrial defibrillator as defined in claim 11 wherein said cardioverting means applies said cardioverting energy to the atria of the heart at a time, following the last pacing of the ventricles for said predetermined number of cardiac cycles, corresponding to said pacing rate.

13. An atrial defibrillator as defined in claim 12 wherein said pacing means also paces the ventricles of the heart coincident with the application of said cardioverting electrical energy to the atria of the heart by said cardioverting means.

14. An atrial defibrillator as defined in claim 11 wherein said predetermined number of paced cardiac cycles is eight paced cardiac cycles.

15. An atrial defibrillator as defined in claim 11 further comprising pacing rate determining means for determining said pacing rate.

16. An atrial defibrillator as defined in claim 15 further including second detecting means for detecting ventricular activations of the heart and wherein said pacing rate determining means is responsive to said second detecting means for determining said pacing rate by averaging the rate of said ventricular activations detected by said second detecting means over a preselected number of cardiac cycles.

17. An atrial defibrillator as defined in claim 16 wherein said pacing rate determining means is further responsive to said atrial fibrillation detecting means for determining said pacing rate prior to the pacing of the ventricles by said pacing means.

18. An atrial defibrillator as defined in claim 16 wherein said preselected number is from ten to twenty.

19. An atrial defibrillator as defined in claim 11 wherein said pacing means paces the ventricles of the heart in a demand mode.

20. An atrial defibrillator as defined in claim 19 wherein said demand mode is a VVI mode.

21. An atrial defibrillator as defined in claim 19 further including pacing rate determining means for providing said pacing means with the pacing rate and wherein said pacing rate determining means incrementally increases the pacing rate for each unpaced cardiac cycle.

22. An atrial defibrillator as defined in claim 21 wherein said demand mode is a VVI mode.

23. An atrial defibrillator as defined in claim 19 wherein said cardioverting means applies the cardioverting electrical energy to the atria of the heart after said pacing means has paced the ventricles for a consecutive said predetermined number of paced cardiac cycles.

24. A method of applying cardioverting electrical energy to the atria of a human heart in need of cardioversion, said method including the steps of:
detecting atrial activity of the heart;
determining when the atria of the heart are in need of cardioversion;
stabilizing the cardiac rate of the heart when the atria of the heart are in need of cardioversion; and
applying said cardioverting electrical energy to the atria of the heart after stabilizing the cardiac rate of the heart for a predetermined number of cardiac cycles.

25. A method as defined in claim 24 wherein said stabilizing step includes pacing the ventricles of the heart.

26. A method as defined in claim 25 wherein said applying step is performed after pacing the ventricles for a predetermined number of cardiac cycles.

27. A method as defined in claim 26 wherein said predetermined number of cardiac cycles are consecutive paced cardiac cycles.

28. A method as defined in claim 25 wherein the ventricles are paced in a demand mode and at a pacing rate.

29. A method as defined in claim 28 wherein said demand mode is a VVI mode.

30. A method as defined in claim 28 including the further step of increasing the pacing rate for each unpaced cardiac cycles.

31. A method as defined in claim 28 including the further step of timing the intervals of the cardiac cycles of the heart and wherein said predetermined number of cardiac cycles is the sum of paced cardiac cycles plus unpaced cardiac cycles having intervals substantially equal to a base interval corresponding to the said pacing rate.

32. A method as defined in claim 31 wherein said unpaced cardiac cycles have intervals between said base interval and ninety percent of said base interval.

33. A method as defined in claim 31 wherein said predetermined number of cardiac cycles are consecutive cardiac cycles.

34. A method of applying cardioverting electrical energy to the atria of a human heart in need of cardioversion, said method including the steps of:
detecting atrial activity of the heart;
determining when the atria of the heart are in need of cardioversion;
pacing the ventricles of the heart at a pacing rate when the atria of the heart are in need of cardioversion; and
applying said cardioverting electrical energy to the atria of the heart after pacing the ventricles of the heart for a predetermined number of paced cardiac cycles.

35. A method as defined in claim 34 wherein said applying step is performed at a time following the last pacing of the ventricles for said predetermined number of paced cardiac cycles corresponding to said pacing rate.

36. A method as defined in claim 35 including the further step of pacing the ventricles of the heart coincident with applying said cardioverting electrical energy to the atria of the heart.

37. A method as defined in claim 34 wherein said predetermined number of paced cardiac cycles is eight paced cardiac cycles.

38. A method as defined in claim 34 including the further steps of detecting ventricular activations of the heart and, prior to pacing the ventricles, determining said pacing rate responsive to the detecting of the ventricular activations of the heart.

39. A method as defined in claim 38 wherein said step of determining said pacing rate includes averaging the rate of the detected ventricular activations over a preselected number of cardiac cycles.

40. A method as defined in claim 39 wherein said preselected number is from ten to twenty.

41. A method as defined in claim 34 wherein said pacing step is performed in a demand mode.

42. A method as defined in claim 41 wherein said demand mode is a VVI mode.

43. A method as defined in claim 41 wherein said pacing step further includes incrementally increasing the pacing rate for each unpaced cardiac cycle.

44. A method as defined in claim 43 wherein said demand mode is a VVI mode.

* * * * *